US006159943A

United States Patent [19]
Butler et al.

[11] Patent Number: 6,159,943
[45] Date of Patent: Dec. 12, 2000

[54] USE OF RIBOSE TO PREVENT CRAMPING AND SORENESS IN MUSCLES

[75] Inventors: Terri Butler, Minneapolis; John St. Cyr, Coon Rapids, both of Minn.

[73] Assignee: Bioenergy, Inc., Ham Lake, Minn.

[21] Appl. No.: 09/405,464

[22] Filed: Sep. 24, 1999

[51] Int. Cl.$^7$ .................................................. A61K 31/70
[52] U.S. Cl. .............................................................. 514/23
[58] Field of Search ................................................ 514/23

[56] References Cited

U.S. PATENT DOCUMENTS

| | | | |
|---|---|---|---|
| 4,605,644 | 8/1986 | Foker | 514/45 |
| 4,719,201 | 1/1988 | Foker | 514/23 |
| 4,824,660 | 4/1989 | Angello et al. | 424/1.1 |
| 4,871,718 | 10/1989 | Carniglia | 514/23 |
| 4,920,098 | 4/1990 | Cotter et al. | 514/2 |
| 4,968,719 | 11/1990 | Brevetti | 514/556 |
| 5,114,723 | 5/1992 | Stray-Gundersen | 426/74 |
| 5,292,538 | 3/1994 | Paul et al. | 426/74 |
| 5,391,550 | 2/1995 | Carniglia et al. | 514/23 |
| 5,707,971 | 1/1998 | Fahy | 514/43 |
| 5,714,515 | 2/1998 | Bunger | 514/557 |

FOREIGN PATENT DOCUMENTS

| | | | |
|---|---|---|---|
| 0573466 | 12/1993 | European Pat. Off. | A61K 31/70 |
| 4228215 | 3/1994 | Germany | 514/23 |

OTHER PUBLICATIONS

Angello, D.A., et al., "Recovery of Myocardial Function and Thallium 201 Redistribution Using Ribose", *American Journal of Cardiac Imaging*, 3 (4), pp. 256–265, (Dec. 1989).

Batista, R., "Partial left ventriculectomy—the Batista procedure", *European Journal of Cardio–Thoracic Surgery*, 15 (Suppl. 1), pp. S12–S19, (Jan. 1999).

Bax, J.J., et al., "Accuracy of Currently Available Techniques for Prediction of Functional Recovery After Revascularization in Patients With Left Ventricular Dysfunction Due to Chronic Coronary Artery Disease: Comparison of Pooled Data", *Journal of the American College of Cardiology*, 30 (6), pp. 1451–1460, (Nov. 15, 1997).

Furnary, A.P., et al., "Multicenter Trial of Dynamic Cardiomyoplasty for Chronic Heart Failure", *Journal of the American College of Cardiology*, 28 (5), pp. 1175–1180, (Nov. 1, 1996).

Gross, M., et al., "Metabolism of D–Ribose Administered Continuously to Healthy Persons and to Patients with Myoadenylate Deaminase Deficiency", *Klin Wochenschr*, 67, pp. 1205–1213, (1989).

Jessup, M., "Optimizing Medical Management of the Patient with Severe Heart Failure Awaiting Cardiac Transplantation", *Cardiology—In Review*, 4(5), pp. 286–291, (Sep. 1996).

Sawada, S.G., et al., "Echocardiographic Detection of Coronary Artery Disease During Dobutamine Infusion", *Circulation*, 83 (5), pp. 1605–1614, (May 1991).

Tullson, P.C., et al., "IMP Metabolism in Human Skeletal Muscle After Exhaustive Exercise", *The American Journal of Physiology*, pp. 146–152, (1995).

Zollner et al, *Klin Wochenschr*, vol. 64, pp. 1281–1290, 1986.

Tullson et al, *American Journal of Physiology*, vol. 261, pp. c342–c347, 1991.

*Primary Examiner*—James H. Reamer
*Attorney, Agent, or Firm*—Schwegman, Lundberg, Woessner & Kluth, P.A.

[57] ABSTRACT

Ribose administered before exercise reduces or prevents exercise-induced muscle cramping and soreness. Ribose taken both before and immediately after exercise further reduces or prevents exercise-induced muscle cramping and soreness.

8 Claims, No Drawings

USE OF RIBOSE TO PREVENT CRAMPING AND SORENESS IN MUSCLES

BACKGROUND OF THE INVENTION

The present invention relates to methods and compositions for the prevention of muscle cramps and soreness. The methods and compositions of the invention are especially suitable for oral administration and are useful for preventing or reducing exercise-induced muscle cramps and soreness.

BACKGROUND OF THE INVENTION

Many persons who exercise vigorously experience muscle cramps and soreness during and after exercise that is uncomfortable, distressing and may lead to an enforced period of inactivity. The degree of exercise that is sufficient to cause these distressing symptoms may vary from person to person. Professional athletes or persons dedicated to physical fitness may exercise extremely hard every day without inducing muscle cramps and soreness. Most persons do not enjoy that level of conditioning. For the average person, exercise is limited to a few times a week, and such persons are often termed "weekend warriors." The limited time available for exercise prevents them from attaining the level of conditioning that allows them to exercise vigorously without muscle cramping and soreness. Persons with reduced pulmonary function may experience these symptoms upon minimal exercise.

The causes of muscle cramping are unknown. It is thought that exercise causes some degree of hypoxia. Among the mechanisms proposed has been the formation of free radicals from the intermediates of adenosine triphosphate breakdown or glycolysis, electrolyte imbalance and lactate formation. The causes of muscle soreness are also unknown. Trauma to the muscle causing loss of myoglobin and electrolytes has also been suggested as a cause, resulting in soreness from the inflammatory response of healing. Regardless of the mechanisms, the need remains for a simple and effective means of preventing or alleviating muscle cramps and soreness.

SUMMARY OF THE INVENTION

The present invention relates to methods and compositions for the prevention and alleviation of muscle cramps and soreness. The present invention provides ribose, alone or in combination with electrolytes and other carbohydrates, to prevent and alleviate muscle cramps and soreness.

DETAILED DESCRIPTION OF THE INVENTION

As is more fully disclosed in pending U.S. patent application Ser. No. 09/290,789, filed Apr. 12, 1999 and titled "COMPOSITION FOR INCREASING ENERGY IN VIVO" (Attorney Docket No. 374.007US1) and a copending patent application filed on the same day as the present application and titled "COMPOSITIONS FOR RAISING THE HYPOXIC THRESHOLD" (Attorney Docket No. 374.011US1), during muscle contraction, oxygen demand may exceed oxygen availability, that is, the muscle may become hypoxic. In exercising, hypoxic muscle, energy production switches from the aerobic to anaerobic production of adenosine triphosphate (ATP). Anaerobic energy production from glucose, that is, glycolysis, produces lactic acid as an end product. At the same time, ATP breaks down to form inosine and hypoxanthine, the further metabolism of which results in the formation of free-radicals, very reactive molecules that can cause cellular damage. Whether the presence of lactate, the damage caused by free radicals or some other mechanism is the primary cause of muscle cramping and soreness is unknown.

As disclosed in the co-pending applications, ribose has been found to be useful in enhancing energy in healthy males or patients with cardiovascular disease or peripheral vascular disease. It has likewise been discovered that the presence of ribose during a hypoxic event can raise the hypoxic threshold in persons encountering situations of low oxygen availability. Here it has been surprisingly discovered that ribose can also relieve exercise-induced muscle cramping and soreness. Without being limited by theory, it is believed that the presence of ribose during exercise relieves the immediate effects of exercise, that is, cramping, while replenishing of ribose in the muscle by the administration of ribose after exercise relieves the later-developing soreness.

This invention provides ribose for the prevention or alleviation of muscle cramping and soreness induced by exercise, alone and in combination with electrolytes and other carbohydrates. This invention also provides doses and protocols for maximum beneficial effect.

Ribose is a simple sugar, with a slightly sweet taste. The amount necessary to prevent cramping is about two to ten grams, or about one-fourth to one teaspoon of dry powder. The powder can be ingested, sprinkled on cereal, or mixed in any convenient liquid, such as water, juice, tea or coffee. Many persons exercising prefer to drink a "replacement" solution such as Gatorade®, Thirst Quencher® or Max®. These sustained energy formulas are generally made up some or all of the following: carbohydrates, including corn syrup, sucrose, fructose and maltodextrin; proteins including casein and soy protein; and lipids, including corn, soy, safflower and canola oils and medium chain triglycerides. Ribose can easily be added to these drinks. Ribose can also be added in an amount sufficient to prevent cramping and muscle soreness to so-called "energy bars such as Balance® or Power Bar®.

We have discovered that it is the presence of ribose during exercise that is effective in preventing cramping. Therefore, whatever the preferred mode of administering ribose, it is important to administer ribose sufficiently ahead of time so that the ribose is delivered to the skeletal muscle during exercise. If ribose is dissolved in a liquid such as water or juice, 15 minutes is sufficient for ribose to be introduced into the circulatory system and delivered to the muscles. If ribose is administered with solid food, absorption may be delayed to as long as one hour. We have discovered that for the best prevention of soreness, it is advisable to take ribose again immediately after exercising. Therefore, it is recommended that ribose be taken both before and immediately after exercising to prevent both cramping and soreness.

The following examples are included to demonstrate preferred embodiments of the invention. In each example, D-Ribose is disclosed as the preferred embodiment. However, it is known to those skilled in the art that certain pentoses such as xylitol and ribulose are readily converted to D-Ribose in vivo. Therefore, the term "ribose" is intended to include D-Ribose and such precursors thereof. It should be appreciated by those skilled in the art that the methods and dosages disclosed in the examples that follow represent methods and dosages discovered by the inventors to function well in the practice of this invention, and thus can be considered to constitute preferred modes for its practice. However, those skilled in the art should, in light of the present disclosure, appreciate that many changes can be made in the specific embodiments that are disclosed and still obtain a like or similar result without departing from the concept and scope of the invention. All such changes are considered to be within the spirit, scope and concept of the invention as defined by the appended claims.

EXAMPLE 1
Long distance runner

An experienced male marathon runner, aged 43, has completed 15 marathons. His training regimen consists of eight- to ten-mile runs, four to five times per week. During the training runs, and especially during and after the marathon races, he has experienced varying degrees of muscle cramping and soreness. He has also felt fatigued after running.

Wishing to obtain the enhancement of energy disclosed in the '789 application, he began taking D-Ribose two to five grams orally three times a day. As expected, he felt an enhancement of energy and unexpectedly, he experienced no muscle cramps. In his next marathon "I was pleasantly surprised by the lack of fatigue and virtually zero cramps. I kept waiting to 'hit the wall' but that never came after training with ribose. In fact I felt very well energized throughout the 26.2 mile run."

EXAMPLE 2
Relief from exercise-induced muscle soreness

A 41-year-old female who jogs two miles once or twice a week experienced exercise-induced muscle soreness, beginning five to ten hours post-exercise and continuing for two or three days. The soreness was severe enough to prevent her from comfortably working out.

She began taking two to five grams D-Ribose in approximately 200 ml of water 15 to 20 minutes before running. After her 20 to 30 minute workout and stretching routine, she took another one gram of D-Ribose dissolved in water. Immediately upon the first beginning to take ribose, she experienced relief from the usual muscle soreness. Whereas, before ribose, she felt soreness beginning at five hours and maximum at 24 hours, after ribose ingestion, she felt only a mild stiffness at 24 hours, insufficient to discourage her from exercising. After she had been taking ribose for a week, she began to experience an increase in energy and a reduction in fatigue.

This subject continues to take ribose before and after workouts in the same doses and continues to experience only mild stiffness and soreness post-exercise and an increase in energy with reduction in fatigue. As a result, she has been able to increase the number of workouts from one to two per week to two to four per week with the added benefit of increased energy and stamina during regular daily activities.

EXAMPLE 3
Relief from muscle cramping in an emphysema patient

An elderly female patient with emphysema experienced muscle cramping and soreness in her hands, legs and feet. These symptoms were exacerbated by even mild exercise. She began taking D-Ribose each morning at a dose of two to four grams. She adjusted the dose according to her anticipated level of activity for the day, taking the higher dose on more active days. She experienced an immediate and total relief from cramping. The relief has been maintained for the four months of ribose ingestion.

EXAMPLE 4
Relief from muscle soreness in a tennis player

A 68-year-old male who plays tennis in weekend tournaments experienced fatigue and sore muscles the day after each game. He found it difficult to play two consecutive days because of soreness, stiffness and fatigue, which prevented him from concentrating well on his games the second day. As a result of these symptoms, he was not able to compete in round-robin tournaments as well as desired. During a weekend tournament held in extremely hot and humid weather, he took three grams of D-Ribose in orange juice after the first day's games. The next day, rather than experiencing the usual soreness and fatigue, he was able to play at peak levels.

All of the compositions and methods disclosed and claimed herein can be made and executed without undue experimentation in light of the present disclosure. While the compositions and methods of this invention have been described in terms of preferred embodiments, it will be apparent to those skilled in the art that variations may be applied to the compositions and methods described herein without departing from the concept and scope of the invention. More specifically, it will be apparent that certain agents that are both chemically and physiologically related may be substituted for the agents described herein while the same of similar results would be achieved. All such similar substitutes and modifications apparent to those skilled in the art are deemed to be within the scope and concept of the invention as defined by the appended claims.

We claim:

1. A method to prevent exercise-induced muscle cramping and soreness in the skeletal muscles of a mammal comprising administering an effective amount of ribose to the mammal a sufficient time prior to exercise so that ribose is present in the skeletal muscle of the mammal during exercise.

2. The method according to claim 1 wherein the amount of ribose is two to 10 grams.

3. The method according to claim 1 wherein the ribose is administered at least ten minutes but no longer than four hours before exercise.

4. A method to prevent exercised induced muscle soreness in a mammal comprising administering an effective amount of ribose to the mammal after exercising.

5. The method according to claim 4 wherein the amount of ribose is one to ten grams.

6. A method to prevent exercise-induced muscle cramping and soreness in the skeletal muscles of a mammal comprising administering a first effective amount of ribose a sufficient time prior to exercise so that ribose is present in the skeletal muscle of the mammal during exercise and administering a second effective amount of ribose immediately after exercise.

7. The method according to claim 6 wherein the first amount of ribose is two to ten grams and the second amount of ribose is one to ten grams.

8. The method of claims 1, 4 or 6 wherein the mammal is a human.

* * * * *